United States Patent
Köcher et al.

(10) Patent No.: US 7,060,817 B2
(45) Date of Patent: *Jun. 13, 2006

(54) SULFONAMIDE ANIONS AS CATALYSTS FOR NCO OLIGOMERIZATION

(75) Inventors: Jürgen Köcher, Langenfeld (DE); Reinhard Halpaap, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/910,943

(22) Filed: Aug. 4, 2004

(65) Prior Publication Data

US 2005/0033005 A1 Feb. 10, 2005

(30) Foreign Application Priority Data

Aug. 7, 2003 (DE) ................. 103 36 186

(51) Int. Cl.
*C07D 229/00* (2006.01)
*C07D 251/34* (2006.01)
*C07D 273/04* (2006.01)

(52) U.S. Cl. .............. 540/202; 252/182.2; 528/51; 528/52; 528/53; 528/57; 528/73; 544/67; 544/68; 544/193; 544/222; 548/951; 548/952

(58) Field of Classification Search ........... 252/182.2; 528/51, 52, 53, 57, 73, 952; 540/202; 544/67, 544/68, 193, 222; 548/951, 952

See application file for complete search history.

(56) References Cited

U.S. PATENT DOCUMENTS

| | | | | |
|---|---|---|---|---|
| 3,582,501 A | | 6/1971 | Hostettler et al. ........... 260/2.5 |
| 3,619,338 A | * | 11/1971 | Gilman et al. .............. 442/251 |
| 4,022,721 A | * | 5/1977 | Ashida ........................ 521/108 |
| 4,059,610 A | * | 11/1977 | Handa et al. ................ 544/193 |
| 4,379,905 A | | 4/1983 | Stemmler et al. ............. 528/73 |
| 4,423,197 A | | 12/1983 | Behr ........................... 526/220 |
| 4,960,848 A | | 10/1990 | Scholl et al. .................. 528/48 |
| 5,410,073 A | * | 4/1995 | Kirchner ..................... 560/357 |
| 5,414,111 A | * | 5/1995 | Kirchner ..................... 560/357 |
| 5,565,564 A | * | 10/1996 | Kirchner ..................... 544/221 |

FOREIGN PATENT DOCUMENTS

| | | |
|---|---|---|
| CA | 1335990 | 6/1995 |
| WO | 86/04911 | 8/1986 |

OTHER PUBLICATIONS

J. Prakt. Chem./Chem. Ztg. 336, 1994, pp. 185-200, Hans Josef Laas et al, "Zur Synthese aliphatischer Polyisocyanate-Lackpolyisocyanate mit Biuret-, Isocyanurat- oder Uretdionstruktur".

Die Angewandt Makromolekulare Chemie, 141, 1986, pp. 173-183, D. Wendisch et al, "Kernresonanzspektroskopische Beiträge zur Struktur und Stereochemie von (cyclo)aliphatischen Isocynaten und deren Folgeprodukten".

* cited by examiner

*Primary Examiner*—Rabon Sergent
(74) *Attorney, Agent, or Firm*—Joseph C. Gil; Thomas W. Roy

(57) ABSTRACT

The present invention relates to the use of sulphonamide salts as catalysts for oligomerizing isocyanates and also to a process for NCO oligomerization using the catalysts of the invention.

4 Claims, No Drawings

SULFONAMIDE ANIONS AS CATALYSTS FOR NCO OLIGOMERIZATION

CROSS REFERENCE TO RELATED PATENT APPLICATION

The present patent application claims the right of priority under 35 U.S.C. §119 (a)–(d) of German Patent Application No. 103 36 186.3, filed Jul. 8, 2003.

FIELD OF THE INVENTION

The present invention relates to the use of sulphonamide salts as catalysts for oligomerizing isocyanates and also to a process for NCO oligomerization using the catalysts of the invention.

BACKGROUND OF THE INVENTION

Since monomeric diisocyanates cannot be used as crosslinkers in polyurethane coating systems, owing to their volatility and toxicological properties, the general approach is to use the higher molecular mass derivatives which are low in monomers, examples being those on a uretdione, isocyanurate, biuret, urethane or allophanate basis. An overview of these polyisocyanates and how to prepare them is given for example in J. Prakt. Chem./Chem. Ztg. 1994, 336, 185–200.

The oligomerization of isocyanates by reacting typically two or three NCO functions with one another leads to the structures of the following formulae 1–3, the uretdione structure (type 1) and the isocyanurate structure (type 2) being the structures which are important industrially.

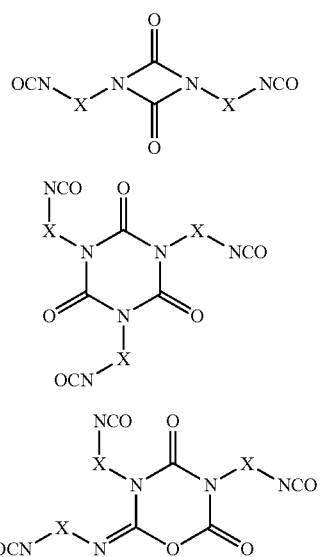

X=carbon skeleton

A multiplicity of covalent and ionic catalysts have been described in the literature as catalysts for this oligomerization (J. Prakt. Chem./Chem. Ztg. 1994, 336, 185–200). Uncharged compounds of covalent construction, however, exhibit a much lower activity than salt-like compounds, so that for a given conversion it is necessary either to use more catalyst or for the reaction time to be longer accordingly.

DE-A 3 100 263, EP-A 339 396 and EP-A 330 966 describe catalysts of salt-like construction, such as carboxylates, fluorides and hydroxides, for isocyanate oligomerization. These catalysts exhibit a high selectivity in respect of formation of isocyanurate (type 2), but hardly any dimer structure (type 1) is formed, or none at all.

SUMMARY OF THE INVENTION

The present invention is directed to a method of oligomerizing isocyanates that includes reacting one or more isocyanate containing compounds in the presence of sulphonamide salts according to formula (I)

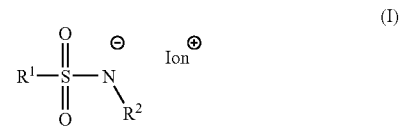

where $R^1$, $R^2$ independently of one another are identical or different aliphatic, cycloaliphatic, aromatic or araliphatic radicals which are optionally branched, substituted and/or heteroatom-contained and $Ion^{(+)}$ is an organic or inorganic cation The present invention is also directed to polyisocyanate compositions obtained by the above-described process, coatings, adhesive bonds or mouldings obtained from such polyisocyanate compositions and substrates coated with the coatings.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about."

It has now been found that sulphonamide salts are likewise highly active NCO oligomerization catalysts, with dimerization and/or trimerization products being obtained and with the ratio of dimer to trimer, in the case of cycloaliphatic isocyanates in particular, being variable within wide limits simply by varying the substituents on sulphur and/or nitrogen.

The invention accordingly provides for the use of sulphonamide salts of the formula (I)

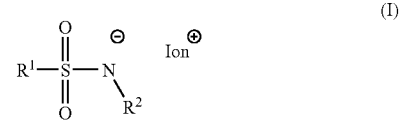

where $R^1$, $R^2$ independently of one another are identical or different aliphatic, cycloaliphatic, aromatic or araliphatic radicals which are optionally branched, substituted and/or heteroatom-contained and $Ion^{(+)}$ is an organic or inorganic cation for oligomerizing isocyanates.

Preferably

R¹ is an optionally branched and/or substituted aliphatic or cycloaliphatic $C_1$–$C_{24}$ radical which optionally contains up to 3 heteroatoms of the elements oxygen, sulphur or nitrogen, R² is a radical of the type already defined in general above for R² and Ion⁽⁺⁾ is an alkali metal or alkaline earth metral cation or an ammonia or phosphonium ion.

Examples of the stated cations for use with preference (Ion⁽⁺⁾) are $Li^+$, $Na^+$ $K^+$, $Mg^{2+}$ and $Ca^{2+}$ and also ammonium and, respectively phosphonium cations of the general formula (II)

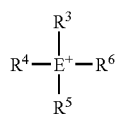

(II)

in which

E is nitrogen or phosphorus and

R³, R⁴ and R⁵ independently of one another are identical or different aliphatic, cycloaliphatic or araliphatic, optionally heteroatom-contained radicals, or hydrogen atom, and R⁶ corresponds to the above definition of R³, R⁴ or R⁵ or to the formula (III)

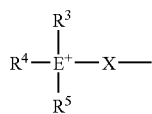

(III)

in which

X is a divalent, optionally heteroatom-contained aliphatic, cycloaliphatic or araliphatic $C_1$–$C_{12}$ radical and R³, R⁴, R⁵ and E are as defined above.

With particular preference

R¹ is an optionally branched aliphatic or cycloaliphatic $C_1$–$C_{18}$ radical which optionally contains up to 3 heteroatoms of the elements oxygen, sulphur, nitrogen and/or optionally contains halogen, cyanide, nitro, alkyl, aryl, alkoxy, aryloxy and/or dialkylamino substituents, R² is a radical which corresponds to the particularly preferred kind of R¹ or is a radical from the group phenyl, tolyl, naphthyl, biphenyl, phenantryl, pyrrolidine, piperidine, piperazine, morpholine, pyrrole, imidazole, pyrazole, indole, indazole, pyridine, pyrimidine, pyridazine, pyrazine, quinoline, isoquinoline, phthalazine, quinoxaline, quinazoline, thiazole, benzothiazole, isothiazole, oxazole, benzoxazole, isothiazole, benzisoxazole, furan, benzofuran, thiophene and benzothiophene, which optionally contains one or more substituents from the group halogen, nitro, cyanide, carboxyl, carboxyalkyl, carboxyaryl, alkyl, aryl, alkoxy, aryloxy and dialkylamino, and Ion⁽⁺⁾ is $Li^+$, $Na^+$, $K^+$ or a monovalent ammonium or phosphonium cation of the general formula (II) in which E is nitrogen or phosphorus and R³, R⁴, R⁵ and R⁶ independently of one another are identical or different aliphatic, cycloaliphatic or araliphatic, optionally heteroatom-contained $C_1$–$C_{18}$ radicals.

With very particular preference

R¹ is a radical of the kind particularly preferred above for R¹,

R² is a radical which corresponds to R¹ or is a radical from the group phenyl, pyrrolidine, piperidine, piperazine, morpholine, 2-pyrimidinyl, 2-thiazolyl, 2-benzthiazolyl, 2-pyrazyl, 2-pyridyl and 4-pyridyl, and Ion(+) is a monovalent cation of the kind particularly preferred above for Ion⁽⁺⁾.

The invention further provides a process for oligomerizing isocyanates wherein a) one or more organic compounds having an average NCO functionality ≧1 are oligomerized in the presence b) of a catalyst comprising one or more sulphonamide salts of the formula (I) and c) optionally solvents.

Into the process of the invention it is possible in component a) to insert all aliphatic, cycloaliphatic, araliphatic and/or aromatic isocyanates that are known to the person skilled in the art and have an NCO functionality ≧1, preferably ≧2, individually or in any desired mixtures with one another, it being immaterial whether they have been prepared by phosgene or phosgene-free processes.

Preference is given to using aliphatic, cycloaliphatic and/or araliphatic isocyanates of the aforementioned kind, having a carbon skeleton (minus the NCO groups present) of 3 to 30, preferably 4 to 20, carbon atoms.

Particularly preferred compounds of component a) correspond to the aforementioned kind having aliphatically and/or cycloaliphatically attached NCO groups, such as, for example, bis(isocyanatoalkyl) ethers, bis- and tris-(isocyanatoalkyl)benzenes, -toluenes, and -xylenes, propane diisocyanates, butane diisocyanates, pentane diisocyanates, hexane diisocyanates (e.g. hexamethylene diisocyanate, HDI), heptane diisocyanates, octane diisocyanates, nonane diisocyanates (e.g. trimethyl-HDI (TMDI) generally as a mixture of the 2,4,4 and 2,2,4 isomers), nonane triisocyanates (e.g. 4-isocyanatomethyl-1,8-octane diisocyanate), decane diisocyanates, decane triisocyanates, undecane diisocyanates, undecane triisocyanates, dodecane diisocyanates, dodecane triisocyanates, 1,3- and 1,4-bis(isocyanatomethyl)cyclohexanes ($H_6$XDI), 3-isocyanatomethyl-3,5,5-trimethylcyclohexyl isocyanate (isophorone diisocyanate, IPDI), bis(4-isocyanatocyclohexyl)methane ($H_{12}$MDI), bis(isocyanatomethyl)norbornane (NBDI) or 3(4)-isocyanatomethyl-1-methylcyclohexyl isocyanate (IMCI).

Especially preferred compounds of component a) are hexamethylene diisocyanate (HDI), trimethyl-HDI (TMDI), 2-methylpentane 1,5-diisocyanate (MPDI), isophorone diisocyanate (IPDI), 1,3- and 1,4-bis(isocyanatomethyl)cyclohexane ($H_6$XDI), bis(isocyanatomethyl)norbornane (NBDI), 3(4)-isocyanatomethyl-1-methylcyclohexyl isocyanate (IMCI) and/or 2,4'- and/or 4,4'-bis(isocyanatocyclohexyl)methane ($H_{12}$MDI) or mixtures of these isocyanates.

The proportional use of monofunctional isocyanates is likewise possible.

In the process of the invention the amount of catalyst b) is from 0.01 to 10 mol %, preferably from 0.05 to 5 mol %, more preferably from 0.1 to 3 mol %, based on the amount of component a), the mol % figures here referring to the overall amount of substance, in mol, of the isocyanate of component a) employed.

As catalyst b) of the process of the invention it is preferred to use exclusively sulphonamide salts of the formula (I).

Catalyst b) can be used undissolved, as the compound per se, or in the form of a solution in the process of the invention. In the latter case the solvent should be chosen such that, while dissolving the catalyst with molecular or ionic dissociation, it does not alter the composition and/or molecular structure of the sulphonamide anion(s) by chemical reactions. At the same time the solvent either must be inert towards NCO functions or may react with isocyanates only with the formation of urea, biuret, urethane or allophanate groups.

Where catalyst b) is used as a solution it is preferred to use straight-chain or branched $C_1$–$C_{20}$, preferably $C_1$–$C_{10}$ alcohols having an OH functionality $\geq 1$ such as, for example, methanol, ethanol, 1- and 2-propanol, the isomeric butanols, 2-ethylhexanol, 2-ethylhexane-1,3-diol, 1,3- and 1,4-butanediol or 1-methoxy-2-propanol.

In one preferred embodiment of the invention catalyst b) is used in the form of a solution.

In the process of the invention it is possible where appropriate to use solvents as component c) as well, though preference is given to using no further solvents as component c), besides the catalyst solvent optionally used.

The process of the invention is carried out preferably at temperatures from 0 to 100° C., more preferably 20 to 100° C.

It will be appreciated that the process if necessary can also be carried out under increased or reduced pressure.

The process of the invention can be conducted either continuously or batchwise. A continuous process comprehends, for example, preparation in a tube reactor or by means of tank cascades, while batchwise processes are, for example, processes in one tank or one flask.

In one preferred embodiment of the invention the NCO oligomerization is taken to a conversion of 10–60 mol %, based on the total amount of NCO groups originally present, the oligomerization reaction is terminated, and unreacted isocyanate is separated off by means, for example, of distillation, optionally under reduced pressure, with the oligomerized isocyanate being obtained in the form of a resin.

Techniques suitable for terminating the oligomerization reaction include in principle all those known to the person skilled in the art (J. Prakt. Chem./Chem. Ztg. 1994, 336, 185–190). These include the removal of the catalyst by means, for example, of extraction or filtration, where appropriate with the assistance of an adsorptive carrier material, the inactivation of the catalyst system by thermal treatment and/or by adding acids or acid derivatives such as benzoyl chloride, phthaloyl chloride, phosphinous, phosphonous or phosphorous acid, phosphinic, phosphonic or phosphoric acid or the acidic esters of the abovementioned phosphorus acids. Preferred terminators are monoalkyl or dialkyl phosphates such as (di)butyl phosphate, (di)octyl phosphate or (di)trihexyl phosphate, sulphuric acid or its acidic esters, or sulphonic acids, such as preferably methanesulphonic acid and p-toluenesulphonic acid, or sulphonic acid esters like p-toluene-sulphonic acid methyl ester.

The amount of the catalyst poison required to terminate the reaction is guided by the amount of the active catalyst. Generally speaking, 70–150 mol % of terminator, based on the amount of catalyst originally employed, is used; preference is given to using equimolar amounts of terminator, based on the amount of catalyst employed.

The polyisocyanates obtained by the process of the invention can be isolated and purified by the customary methods of the state of the art, such as thin-film distillation, extraction, crystallization and/or molecular distillation, for example. They are obtained as colourless or only slightly coloured liquids or solids.

A particular advantage of the catalysts of the invention for isocyanate oligomerization is their high selectivity for the formation of isocyanurate and, where appropriate, at the same time uretdione; they are highly active in this context, and few if any iminooxadiazinedione fractions are formed. In the case of the cycloaliphatic isocyanates in particular the catalysts of the invention additionally exhibit a propensity to form NCO dimers which is surprisingly high for ionic catalysts.

The polyisocyanates prepared in accordance with the invention represent starting materials with diverse possible uses for the preparation of polymers, such as foamed or unfoamed plastics or polyurethane paints, for example, especially for preparing one- and two-component polyurethane paints, coatings, adhesives and adjuvants for application to materials such as wood, plastic, leather, metal, paper, concrete, masonry, ceramic and textile, for example.

EXAMPLES

The percentages for the conversion are calculated by dividing the amount of isocyanate converted by the total amount of isocyanate employed multiplied by 100. All other percentage figures are to be understood, unless noted otherwise, as percentages by weight.

The NCO content of the resins described in the inventive and comparative examples was determined by titration in accordance with DIN 53 185.

Abbreviations Used:

DMSO: dimethyl sulphoxide n-Bu or Bu: n-butyl i-PrOH: isopropanol

The dynamic viscosities of the polyisocyanate resins were determined at 23° C. using the viscometer VT 550, cone and plate measurement setup PK 100, from Haake (Karlsruhe, Germany). Measurements at different shear rates ensured that the rheology of the polyisocyanate mixtures of the invention described, like that of the comparison products, corresponds to that of ideal Newtonian liquids. It is therefore unnecessary to state the shear rate.

To determine the isocyanate conversion 20 to 40 mg of the reaction mixtures prepared were dissolved in 3 ml of chloroform and analyzed by gel permeation chromatography (column MZ-Gel Sdplus 500A 5 μm, MZ-Analysentechnik, Mainz, Germany). Owing to the high level of dilution of the measurement solution there was no need to deactivate the catalyst. The NCO conversion or resin yield can be calculated from the amount of monomeric isocyanate found. Subsequent determination of the selectivity of the catalyst used was carried out by analysing the formed structural types 1–3. This was done by subjecting 30 μl of the reaction mixture to measurement between KBr plates by IR spectroscopy (spectrometer: Arid-Zone® from Bomem, Quebec, Canada, scan count 10, resolution 2 $cm^{-1}$). The vibrations at 1760 $cm^{-1}$ (structural type 1), 1690 $cm^{-1}$ (structural type 2) and 1780 $cm^{-1}$ (structural type 3) can be used to demonstrate the formation of structural types 1–3. Where more than one structural type alone was formed, $^{13}C$-NMR measurements were carried out for quantitative evaluation and the quantities of product were calculated by signal integration.

For the $^{13}C$-NMR analysis 0.5 ml of each reaction mixture was admixed with stoichiometric amounts (based on the amounts of catalyst employed) of di-n-butyl phosphate in order to deactivate the catalyst and prevent further reaction. Deuterated chloroform was added to give a concentration of approximately 50% by weight resin. Measurements were made on a DPX 400 from Bruker, Karlsruhe, Germany at a $^{13}C$ resonance frequency of 100 MHz. The reference used for the ppm scale was tetramethylsilane, as internal standard.

Data for the chemical shift of the compounds in question are taken from the literature (cf. Die Angewandte Makromolekulare Chemie 1986, 141, 173–183 and references cited therein) and/or obtained by subjecting model substances to measurement.

Preparation of Inventive Catalysts

Example 1

Preparation of n-butyl-N-n-propylsulfonamide 6.9 ml of n-propylamine (4.9 g, 84 mmol) and 11.6 ml of triethylamine (8.5 g, 84 mmol) were dissolved at room temperature in 85 ml of methylene chloride. Likewise at room temperature 10.9 ml of n-butanesulfonyl chloride (13.1 g, 84 mmol) were added dropwise to this solution over the course of 1 h. After 20 h of stirring the reaction mixture was washed twice with 50 ml of water. The organic phase was dried over magnesium sulphate, the methylene chloride was distilled off and the oily residue which remained was dried in vacuo. This gave 13.5 g of the target compound, whose constitution was verified by NMR spectroscopy.

Example 2

Preparation of n-butyl-N-(2-methoxyethyl)sulfonamide 6.4 ml of 2-methoxyethylamine (5.5 g, 73.7 mmol) and 10.2 ml of triethylamine (7.4 g, 73.7 mmol) were dissolved at room temperature in 72 ml of methylene chloride. Likewise at room temperature 9.6 ml of n-butanesulfonyl chloride (11.5 g, 73.7 mmol) were added dropwise to this solution over the course of one hour. After 1 h of stirring at room temperature the reaction mixture was washed twice with 100 ml of water. The organic phase was dried over magnesium sulphate, the methylene chloride was distilled off and the oily residue which remained was dried in vacuo. This gave 12.4 g of the target compound, whose constitution was verified by NMR spectroscopy.

Example 3

Preparation of n-butyl-N4-methylpiperazinylsulfonamide 8.9 ml of 1-amino-4-methylpiperazine (8.5 g, 73.7 mmol) and 10.2 ml of triethylamine (7.4 g, 73.7 mmol) were dissolved at room temperature in 72 ml of methylene chloride. Likewise at room temperature 9.6 ml of n-butanesulfonyl chloride (11.5 g, 73.7 mmol) were added dropwise to this solution over the course of one hour. After 22 h of stirring at room temperature the reaction mixture was washed twice with 100 ml of water. The organic phase was dried over magnesium sulphate, the methylene chloride was distilled off and the oily residue which remained was dried in vacuo. This gave 11.6 g of the target compound, whose constitution was verified by NMR spectroscopy.

Example 4

Preparation of n-butyl-N-isoxazolosulfonamide 6.2 g of 3-aminoisoxazole (73.7 mmol) and 10.2 ml of triethylamine (7.4 g, 73.7 mmol) were dissolved at room temperature in 72 ml of THF. Again at room temperature 9.6 ml of n-butanesulfonyl chloride (11.5 g, 73.7 mmol) were added to this solution over the course of one hour. After 22 h of stirring at room temperature the reaction mixture was diluted with 200 ml of methylene chloride, then extracted by shaking twice with 200 ml of 1 N NaOH. The aqueous phase was carefully adjusted to a pH of 1–2 using concentrated HCl and then extracted twice with 100 ml of methylene chloride. After drying over magnesium sulphate, the organic phase was freed from the solvent and the oily residue was dried in vacuo. This gave 7.8 g of the target compound, whose constitution was verified by NMR spectroscopy.

Example 5

Preparation of n-butyl-N-2-thiazolylsulfonamide 7.4 g of 2-aminothiazole (73.7 mmol) and 10.2 ml of triethylamine (7.4 g, 73.7 mmol) were dissolved at room temperature in 100 ml of THF. Again at room temperature 9.6 ml of n-butanesulfonyl chloride (11.5 g, 73.7 mmol) were added dropwise to this solution over the course of one hour. After 21 h of stirring at room temperature a further 4 ml of n-butanesulfonyl chloride (4.8 g, 30.8 mmol) were added and stirring was continued at room temperature for 20 h. The reaction mixture was washed twice with 100 ml of 1 N NaOH and then washed to neutrality (pH 6–7) with water. The organic phase was dried over magnesium sulphate and then freed from the solvent. The 9.0 g of crude product obtained were recrystallized from 80 ml of tert-butyl methyl ether. This gave 3.2 g of the target compound, whose constitution was verified by NMR spectroscopy.

Example 6

Preparation of n-butyl-N-morpholinosulfonamide 3.8 g of N-aminomorpholine (36.9 mmol) and 5.1 ml of triethylamine (3.7 g, 36.9 mmol) were dissolved at room temperature in 40 ml of methylene chloride. Again at room temperature 4.8 ml of n-butanesulfonyl chloride (5.8 g, 36.9 mmol) were added dropwise to this solution over the course of one hour. After 20 h of stirring at room temperature the reaction mixture was extracted by shaking twice with 50 ml of water and the organic phase was dried over magnesium sulphate and concentrated. The 6.7 g of crude product obtained were recrystallized from 30 ml of tert-butyl methyl ether. The constitution of the target compound was verified by NMR spectroscopy.

Example 7

Preparation of n-butyl-N-pyrazinosulfonamide 7.0 g of aminopyrazine (73.7 mmol) and 10.2 ml of triethylamine (7.4 g, 73.7 mmol) were dissolved at room temperature in 72 ml of methylene chloride. Again at room temperature 9.6 ml of n-butanesulfonyl chloride (11.5 g, 73.7 mmol) were added dropwise to this solution over the course of 1 h. After 20 h of stirring at room temperature the batch was admixed with 100 ml of water and then extracted twice with 200 ml of methylene chloride. The organic phase was washed once with 100 ml of water and then dried over magnesium sulphate. The crude product in 200 ml of methylene chloride was extracted with 200 ml of 1 N NaOH. The aqueous phase was adjusted to a pH of 1–2 using concentrated HCl and then extracted with 200 ml of methylene chloride. The organic phase was dried over magnesium sulphate and concentrated. This gave 4.0.g of the target compound, whose constitution was verified by NMR spectroscopy.

Example 8

Preparation of n-butyl-N-phenylsulfonamide 9.9 ml of aniline (10.1 g, 108.4 mmol) and 15 ml of triethylamine (11.0 g, 108.4 mmol) were dissolved at 50° C. in 108 ml of methylene chloride. Again at 50° C. 14.1 ml of n-butanesulfonyl chloride (17.0 g, 108.4 mmol) were added dropwise to this solution over the course of 1 h. After 15 minutes of stirring at 50° C. the reaction mixture was extracted twice with 100 ml of water. The resultant crude product in solution in 150 ml of methylene chloride was extracted with 150 ml of 1 N NaOH. The aqueous phase was adjusted to a pH of 1–2 using concentrated HCl and was extracted twice with 100 ml of methylene chloride. Drying over magnesium sulphate and removal of the methylene chloride by distillation gave 17.0 g of the target compound, whose constitution was verified by NMR spectroscopy.

Example 9

Synthesis of the Tetrabutylammonium Salt of the n-butyl-N-n-propylsulfonamide Anion A solution of 6.7 g of n-butyl-N-n-propylsulfonamide (37.3 mmol) from Example 1 in 7.5 ml of methanol was added dropwise at room temperature to 7.1 ml of a 30% strength Na methoxide solution (37.3 mmol). Stirring was continued at room temperature for one hour and then 16.9 g of a 61.4% strength solution of tetrabutylammonium chloride (37.3 mmol) in isopropanol was added dropwise. The mixture was stirred at room temperature for one hour more and then the precipitated NaCl was filtered off. The filtrate was freed from the solvent in vacuo. The residue was dried in vacuo to remove final solvent residues. This gave 14.1 g of an oily product. The constitution of the target compound was verified by NMR spectroscopy.

Examples 10–15

By procedure in analogy to example 9 the tetrabutylammonium salts of the sulfonamides from examples 2, 3 and 5–8 were prepared and were characterized by NMR spectroscopy.

Example 16

Synthesis of the Tetrabutylphosphonium Salt of the n-butyl-N-n-propylsulfonamide Anion A solution of 6.7 g of n-butyl-N-n-propylsulfonamide (37.3 mmol) from example 1 in 7.5 ml of methanol was added dropwise at room temperature to 7.1 ml of a 30% strength Na methoxide solution (37.3 mmol). Stirring was continued at room temperature for one hour and then 15.4 g of a 71.4% strength solution of tetrabutylphosphonium chloride (37.3 mmol) in isopropanol was added dropwise. The mixture was stirred at room temperature for one hour more and then the precipitated NaCl was filtered off. The filtrate was freed from the solvent in vacuo. The residue was dried in vacuo to remove final solvent residues. This gave 16.6 g of an oily product. The constitution of the target compound was verified by NMR spectroscopy.

Examples 17–22

By procedure in analogy to example 16 the tetrabutylphosphonium salts of the sulfonamides from examples 2, 3 and 5–8 were prepared and were characterized by NMR spectroscopy.

Example 23

Synthesis of tri-n-butyltetradecylphosphonium Salt of n-butyl-N-phenylsulfonamide Anion A solution of 2.2 g of n-butyl-N-phenylsulfonamide (10.5 mmol) from example 8 in 7 ml of methanol was added dropwise at room temperature to 2 ml of a 30% strength Na methoxide solution (10.5 mmol). Stirring was continued at room temperature for one hour and then 4.6 g of tri-n-hexyltetradecylphosphonium chloride (10.5 mmol) was added dropwise. The mixture was stirred at room temperature for one hour more and then the precipitated NaCl was filtered off. The filtrate was freed from the solvent in vacuo. The residue was dried in vacuo to remove final solvent residues. This gave 5.2 g of an oily product. The constitution of the target compound was verified by NMR spectroscopy.

Example 24

By procedure in analogy to example 23 the tri-n-butyltetradecylphosphonium salt of the sulfonamide from example 7 were prepared. Characterization took place by NMR spectroscopy.

Example 25

Synthesis of tri-n-hexyltetradecylphosphonium Salt of n-butyl-N-phenylsulfonamide Anion A solution of 2.2 g of n-butyl-N-phenylsulfonamide (10.5 mmol) in 7 ml of methanol was added dropwise at room temperature to 2 ml of a 30% strength Na methoxide solution (10.5 mmol). Stirring was continued at room temperature for one hour and then 5.4 g of tri-n-hexyltetradecylphosphonium chloride (10.5 mmol) was added dropwise. The mixture was stirred at room temperature for one hour more and then the precipitated NaCl was filtered off. The filtrate was freed from the solvent in vacuo. The residue was dried in vacuo to remove final solvent residues. This gave 6.3 g of an oily product. The constitution of the target compound was verified by NMR spectroscopy.

Example 26

By procedure in analogy to example 25 the tri-n-hexyltetradecylphosphonium salt of the sulfonamide from example 7 were prepared. The constitution of the target compound was verified by NMR spectroscopy.

Examples 27 to 29

Inventive Oligomerization Reactions

General Instruction

The amounts of pure catalyst indicated in Examples 27 to 29 of Tables 1 to 3 were weighed out into a glass vessel with a septum seal. The vessel was then evacuated twice and filled with argon. A syringe was used subsequently to add the amounts of diisocyanate indicated likewise in Examples 27–29 of Tables 1–3 via the septum.

Where the catalyst was used as a solution (Examples 27 c, d, e, f; 28 c, d, h, i; 29 a, b, g, h) the reaction vessel with septum seal was evacuated twice and filled with argon. A syringe was used to introduce 5 ml of each diisocyanate into the vessel thus prepared, after which the corresponding amounts of catalyst in the solvent stated were added with stirring.

The reaction mixture obtained was subsequently reacted under the conditions indicated in the following tables in an oil bath or in a stirred heating block (e.g. Variomag reaction block type 48.2/RM from H&P Labortechnik GmbH, Oberschleißheim, Germany).

Subsequent analysis was carried out as indicated above.

TABLE 1

Results of the inventive HDI oligomerization

| Ex. | Cat. | Amount [mol %] | Form used | Time [h] | T. [° C.] | Conversion [%] | Type 1 [mol %] | Type 2 [mol %] |
|---|---|---|---|---|---|---|---|---|
| 27a | 15 | 0.025 | 100% | 0.33 | 40 | 50 | 0 | 100 |
| 27b | 22 | 0.025 | 100% | 0.25 | 40 | 37 | 0 | 100 |
| 27c | 14 | 0.75 | 1 M/i-PrOH | 1.5 | 40 | 63 | 0 | 100 |
| 27d | 21 | 0.75 | 1 M/i-PrOH | 1 | 40 | 50 | 0 | 100 |
| 27e | 24 | 0.3 | 2 M/i-PrOH | 4 | 40 | 36 | 0 | 100 |
| 27f | 26 | 0.4 | 2.2 M/i-PrOH | 4 | 40 | 34 | 0 | 100 |

TABLE 2

Results of the inventive IPDI oligomerization

| Ex. | Cat. | Amount [mol %] | Form used | Time [h] | T [° C.] | Conversion [%] | Type 1 [mol %] | Type 2 [mol %] |
|---|---|---|---|---|---|---|---|---|
| 28a | 16 | 0.45 | 100% | 4 | 40 | 31 | 0 | 100 |
| 28b | 17 | 0.3 | 100% | 1 | 40 | 41 | 0 | 100 |
| 28c | 18 | 0.75 | 1 M/DMSO | 3 | 40 | 49 | 30 | 70 |
| 28d | 18 | 1.0 | 1 M/DMSO | 3 | 40 | 52 | 23 | 77 |
| 28e | 12 | 1.5 | 100% | 92 | 40 | 28 | 46 | 54 |
| 28f | 12 | 2.0 | 100% | 92 | 40 | 42 | 42 | 58 |
| 28g | 19 | 2.0 | 100% | 72 | 40 | 43 | 46 | 54 |
| 28h | 13 | 0.13 | 0.5 M/DMSO | 0.4 | 40 | 65 | 14 | 86 |
| 28i | 13 | 0.15 | 0.5 M/DMSO | 0.4 | 40 | 74 | 14 | 86 |
| 28j | 20 | 1.5 | 100% | 1 | 40 | 85 | 40 | 60 |
| 28k | 15 | 0.2 | 100% | 1 | 40 | 41 | 0 | 100 |
| 28l | 22 | 0.75 | 100% | 47 | 40 | 31 | 49 | 51 |
| 28m | 22 | 1.0 | 100% | 47 | 40 | 40 | 46 | 54 |
| 28n | 24 | 1.0 | 100% | 48 | 40 | 42 | 37 | 63 |

TABLE 3

Results of the inventive $H_{12}MDI$ oligomerization

| Ex. | Cat. | Amount [mol %] | Form used | Time [h] | T [° C.] | Conversion [%] | Type 1 [mol %] | Type 2 [mol %] |
|---|---|---|---|---|---|---|---|---|
| 29a | 9 | 0.15 | 1 M/i-PrOH | 1.5 | 40 | 30 | 0 | 100 |
| 29b | 16 | 0.25 | 1 M/i-PrOH | 6 | 40 | 22 | 0 | 100 |
| 29c | 10 | 0.75 | 100% | 0.58 | 40 | 37 | 28 | 72 |
| 29d | 10 | 1.0 | 100% | 0.58 | 40 | 55 | 32 | 68 |
| 29e | 17 | 1.0 | 100% | 47 | 40 | 40 | 33 | 67 |
| 29f | 17 | 2.0 | 100% | 47 | 40 | 40 | 37 | 63 |
| 29g | 11 | 0.13 | 1 M/i-PrOH | 3 | 40 | 34 | 0 | 100 |
| 29h | 13 | 0.2 | 0.5 M/DMSO | 5 | 40 | 53 | 0 | 100 |
| 29i | 15 | 0.25 | 100% | 17 | 40 | 53 | 0 | 100 |

Comparative Examples 1 to 3

The reactions of HDI, IPDI and $H_{12}MDI$ were carried out in accordance with EP-A 0 010 589 using benzyltrimethylammonium hydroxide in solution in methanol (Triton®B, Aldrich) in analogy to the procedure of the inventive examples:

Comparative Examples 1a: Reaction of HDI

| Ex. | Catalyst | Amount [mol %] | Time [h] | T [° C.] | Conversion [%] | Type 1 [mol %] | Type 2 [mol %] | Type 3 [mol %] |
|---|---|---|---|---|---|---|---|---|
| 1a | Triton ® B | 0.035 | 0.25 | 60 | 42.7 | 2.1 | 94.4 | 3.5 |

Comparative Example 2a: Reaction of IPDI

| Ex. | Catalyst | Amount [mol %] | Time [h] | T [° C.] | Conversion [%] | Type 1 [mol %] | Type 2 [mol %] |
|---|---|---|---|---|---|---|---|
| 2a | Triton® B | 0.18 | 1 | 40 | 48.6 | 0 | 100 |

Comparative Example 3a: Reactions of $H_{12}MDI$

| Ex. | Catalyst | Amount [mol %] | Time [h] | T [° C.] | Conversion [%] | Type 1 [mol %] | Type 2 [mol %] |
|---|---|---|---|---|---|---|---|
| 3a | Triton® B | 0.2 | 21.5 | 40 | 51.7 | 1.2 | 98.8 |

As can be seen, the tetraalkylammonium hydroxide of salt-like construction is highly active but yields only low uretdione fractions in the product mixture. In the case of the HDI reaction, indeed, a distinct formation of iminooxadiazinedione structures can be observed. In contrast the catalysts of the invention, as a function of their substitution pattern on sulphur and nitrogen, provide very variable proportions of uretdione/isocyanurate with a likewise very high catalytic activity. When reacting the linear-aliphatic HDI, furthermore, an impressively high selectivity with respect to the isocyanurate structure is observed, with the formation of the asymmetric trimer (type 3) being completely absent at the same time.

Example 30

Process Example

Trimerization of 4,4'-diisocyanatodicyclohexylmethane
500 g (1.91 mol) of 4,4'-diisocyanatodicyclohexylmethane were degassed in vacuo (2 mbar) for 30 minutes and then gassed with dry nitrogen and heated to 60° C. With stirring, 2.3 g (3.3 mmol) of a 60% strength solution of the catalyst from Example 9 in 2-ethyl-1,3-hexandiol were added over a period of 1 hour at a rate such that the temperature in the reaction mixture did not exceed 70° C. After the end of addition of catalyst the trimerization reaction was terminated by addition of 0.7 g (3.3 mmol) of dibutyl phosphate. The NCO content of the mixture was 25.8%, corresponding to a degree of oligomerization of 19.0%. The clear, pale yellow crude solution is then admixed with 26.5 g of an isocyanurate polyisocyanate based on HDI, obtained according to Example 12 of EP-A 330 966, and then is freed as described in Example 2 from excess 4,4'-diisocyanatodicyclohexylmethane by thin-film distillation. The solid resin obtained was dissolved with a mixture of 1-methoxyprop-2-yl acetate and xylene (1:1) and adjusted to a solids content of 70%. This gave a pale, clear polyisocyanate solution having an NCO content of 10.4%, a monomeric 4,4'-diisocyanatodicyclohexylmethane content of 0.2% and a viscosity (23° C.) of 6.060 mPas.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of oligomerizing isocyanates comprising reacting one or more isocyanate containing compounds in the presence of sulphonamide salts according to formula (I)

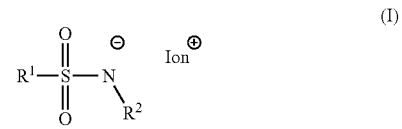

where
R$^1$, R$^2$ independently of one another are identical or different aliphatic, cycloaliphatic, aromatic or araliphatic radicals which are optionally branched, substituted and/or heteroatom-contained and
Ion$^+$ is an organic or inorganic cation.

2. The method according to claim 1, wherein
R$^1$ is an optionally branched aliphatic or cycloaliphatic $C_1$–$C_{18}$ radical which optionally contains up to 3 heteroatoms of the elements oxygen, sulphur and nitrogen and/or optionally contains halogen, cyanide, nitro, alkyl, aryl, alkoxy, aryloxy and/or dialkylamino substituents,
R$^2$ is a radical as defined for R$^1$ or is phenyl, pyrrolidine, piperidine, piperazine, morpholine, 2-pyrimidinyl, 2-thiazolyl, 2-benzthiazolyl, 2-pyrazyl, 2-pyridyl or 4-pyridyl, and
Ion(+) is Li$^+$, Na$^+$ or K$^+$ or a monovalent ammonium or phosphonium cation of the general formula (II)

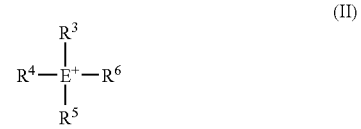

in which
E is nitrogen or phosphorus and
R$^3$, R$^4$, R$^5$ and R$^6$ independently of one another are identical or different aliphatic, cycloaliphatic or araliphatic, optionally heteroatom-contained $C_1$–$C_{18}$ radicals.

3. The method according to claim 1, wherein
a) one or more organic compounds having an average NCO functionality ≧ 1 are oligomerized in the presence
b) of a catalyst comprising one or more sulphonamide salts, and
c) optionally solvents.

4. The method according to claim 3, wherein the NCO oligomerization is carried out at a temperature of 20 –100° C. until 10 –60 mol % of all the NCO groups have undergone conversion and then the oligomerization reaction is terminated by addition of a catalyst poison and unreacted monomeric isocyanate is separated off by distillation.

* * * * *